United States Patent [19]

Kesling

[11] Patent Number: 5,269,682

[45] Date of Patent: Dec. 14, 1993

[54] METHOD FOR IDENTIFYING AND REMOVING ORTHODONTIC BONDING ADHESIVE

[75] Inventor: Christopher K. Kesling, LaPorte, Ind.

[73] Assignee: TP Orthodontics, Inc., Westville, Ind.

[21] Appl. No.: 7,583

[22] Filed: Jan. 22, 1993

[51] Int. Cl.$^5$ ............................................. A61C 3/00
[52] U.S. Cl. ............................................. 433/24; 433/9
[58] Field of Search ........................................ 433/9, 24

[56] References Cited

U.S. PATENT DOCUMENTS

| | | | |
|---|---|---|---|
| 2,377,382 | 6/1945 | Slack, Jr. | 433/203.1 |
| 3,309,274 | 3/1967 | Brilliant | 106/35 |
| 3,955,282 | 5/1976 | McNall | 433/9 |
| 4,063,360 | 12/1977 | Waller | 433/9 |
| 4,167,417 | 9/1979 | Franz et al. | 106/35 |
| 4,435,160 | 3/1984 | Randklev | 433/9 |
| 4,479,782 | 10/1984 | Orlowski et al. | 433/9 |
| 4,517,172 | 5/1985 | Southard | 424/49 |
| 4,554,336 | 11/1985 | Kidd et al. | 526/301 |
| 4,645,455 | 2/1987 | Kosmos | 433/203.1 |
| 4,749,352 | 6/1988 | Nicholson | 433/9 |
| 4,906,185 | 3/1990 | Randklev | 433/8 |
| 4,952,142 | 8/1990 | Nicholson | 433/9 |
| 5,049,068 | 9/1991 | Sterrett et al. | 433/9 |
| 5,096,417 | 3/1992 | Greenberg et al. | 433/24 |
| 5,154,613 | 10/1992 | Cohen | 433/9 |

Primary Examiner—John J. Wilson
Attorney, Agent, or Firm—Lloyd L. Zickert

[57] ABSTRACT

A method to aid in the identification and removal of orthodontic attachment adhesives characterized by incorporating a fluorescent agent in the adhesive and inspecting the oral cavity with ultraviolet light which excites the fluorescent agent by which the excess adhesive can be recognized and removed by a dental tool.

5 Claims, No Drawings

METHOD FOR IDENTIFYING AND REMOVING ORTHODONTIC BONDING ADHESIVE

DESCRIPTION

This invention relates to orthodontics and in particular to a method of detecting displacements (excess) of a bonding adhesive used to anchor an orthodontic bracket, as well as the presence of residual adhesive when the bracket is debonded.

BACKGROUND OF THE INVENTION

The bonding of attachments to teeth, such as brackets, molar tubes, retentive devices and functional appliances, is well known. The bracket, bonded by an adhesive to teeth, allows one or more wires to be anchored to the bracket so that forces may be applied for correcting the positions of teeth.

Excess adhesive needs to be removed, not only for cosmetic purposes, but for other reasons as well. Excess adhesive affords niches for bacteria. The excess is annoying especially if hardened between the teeth. Bonding material in the archwire slot interferes with the interaction of the wire and bracket. The present invention is concerned with facilitating removal of excess bonding adhesive following emplacement of the bracket, and for facilitating removal of residual adhesive left on teeth after brackets or other bonded attachments have been debonded.

Heretofore, it has been known to use fluorescent agents in dental composites for certain purposes such as to detect plaque-like deposits, and to produce a restored tooth that will fluoresce.

SUMMARY OF THE INVENTION

The present invention overcomes the problems of excess and residual adhesive by enabling the detection of same by use of ultraviolet light energy.

A fluorescent agent is mixed with an orthodontic bracket bonding adhesive in sufficient quantity to render any excess or residual occlusions or specks of adhesive highly emissive (fluorescent glow) when irradiated by an ultraviolet light source which itself is intensive enough to excite the agent to fluorescence. The excess or residual can be removed by an appropriate dental tool.

It is therefore an object of the present invention to provide a bonding adhesive that will be visible under an ultraviolet light source to enhance bonding and debonding procedures to remove excess and residual adhesive.

Other objects, features and advantages of the invention will be apparent from the following detailed disclosure.

DESCRIPTION OF THE INVENTION

Fluorescent dyes such as fluorescein or 2,5-Bis (5-t-butylbenzoazolyl- 2)-thiophene (BBOT) can be mixed in minute quantities into acrylic based epoxy adhesives. The addition of these dyes does not harm the long term stability nor total bond strength to any significant value.

Upon curing, the epoxies show no appreciable color change in white light and have been tested for cytotoxicity in rats, with no negative effects. Predicted shelf life of such dyes locked into an acrylic matrix, in the dark confines of the oral cavity, would be two or more years.

Under influence of long wave ultra-violet light (UV) centered around 360 nm and at power levels of 300 micro watts per square cm, a vivid color presentation occurs in the visible portion of the spectrum. In the case of BBOT, under the influence of UV excitation, broadband emission occurs at 430 nm. Fluorescein under the same conditions will fluoresce in the region of 540 nm. Both of these dyes are in the chemical family of oxazoles.

The initial choice of these dyes was made following the criteria of nil toxicity, high solubility in the epoxy base, good dispersion within the epoxy matrix to minimize leaching effects and efficient conversion of UV excitation into prominent, visible wavelengths.

The present invention is both a method and material utilized for bonding and debonding of dental brackets used in orthodontic treatment and may be used in conjunction with preferred metal, ceramic, plastic or composite dental brackets. During the process of bonding dental brackets to teeth, an epoxy bracket bonding adhesive in liquid or gel form is applied to the base of the bracket. The bracket is then applied to the tooth surface and the epoxy allowed to cure, forming a preferred chemical/mechanical bond. If excessive amounts are used during the process, this material will squeeze out well beyond the area of the bonding base. Such a condition provides a surface for the accumulation of plaque and debris not readily removable via normal oral hygiene.

If during the process of bonding a fluorescent agent contained within the bonding epoxy were used in conjunction with a low power UV long wave light source to illuminate the oral cavity, the excess material around the base of the bracket would be readily seen, and in a liquidus state easily removed prior to cure of the bond. This in turn would assure uniformity in application of the bonding layer as well as an aesthetically pleasing bonding area. In the case of transparent brackets such as plastics or ceramic, it would also be possible to view the area under the bracket base as being completely coated and with out air entrapment. A uniform fluorescent intensity would indicate a uniform coverage of the bracket base, further insuring maximum bond strength for the length of the treatment. It would be possible, via UV inspection, to detect fractures in the adhesive during the treatment before catastrophic adhesive failure occurs.

Thus, after emplacement of the bracket to the tooth has been achieved, the oral cavity may be illuminated with UV light to excite the fluorescent agent to its emissive state (fluorescing state). Excess specks and interdental deposits may be removed before the epoxy bonding layer has set (cured). Illumination and inspection of the oral cavity can be accomplished by ultraviolet light devices of penlight configuration.

Thus far, the fluorescent dyes BBOT and fluorescein have been utilized in orthodontic epoxies such as TP Orthodontics, Inc. RIGHT-ON, ONE-TO-ONE, UL-TRALIGHT. A blue light-cured epoxy especially formulated with these dyes has shown no changes in physical and mechanical characteristics.

While two dyes of preference are disclosed, there are undoubtedly others which will serve the same purpose.

It will be understood that modifications and variations may be effected without departing from the scope of the novel concepts of the present invention, but it is understood that this application is to be limited only by the scope of the appended claims.

The invention is hereby claimed as follows:

1. A method of identifying and effecting removal of excess and residual orthodontic attachment bonding adhesive in which the adhesive cures from a liquid or gel form to a solid state and contains a fluorescent dye comprising the following steps:
   (a) employing the adhesive in bonding an attachment to a tooth;
   (b) illuminating the oral cavity with light having a wavelength which will excite the fluorescent agent to its emissive state;
   (c) relying on the emissive state of the fluorescent agent to inspect the oral cavity incidental to removal of excess and residual adhesive; and
   (d) removing the excess and residual adhesive.

2. Method according to claim 1 in which excess adhesive is removed before the adhesive cures.

3. Method according to claim 1 in which excess adhesive is removed after the adhesive has cured.

4. Method according to claim 1 including the additional step of inspecting and correcting the bonding layer for uniformity after the attachment is emplaced but before the adhesive has cured.

5. Method according to claim 1 in which the adhesive is an epoxy and in which the fluorescent agent is selected from the group consisting of fluorescein and 2,5-Bis(5-t-butylbenzoazolyl-2)-thiophene.

* * * * *